(12) United States Patent
Bystryak et al.

(10) Patent No.: US 9,097,712 B2
(45) Date of Patent: Aug. 4, 2015

(54) FLOW-THROUGH CELL COUNTING ASSAY

(71) Applicant: Allied Innovative Systems, LLC, Budd Lake, NJ (US)

(72) Inventors: Simon Bystryak, Budd Lake, NJ (US); Rasa Santockyte, Princeton, NJ (US)

(73) Assignee: Allied Innovative Systems LLC, Budd Lake, NJ (US)

( * ) Notice: Subject to any disclaimer, the term of this patent is extended or adjusted under 35 U.S.C. 154(b) by 61 days.

(21) Appl. No.: 13/863,490

(22) Filed: Apr. 16, 2013

(65) Prior Publication Data

US 2014/0273018 A1    Sep. 18, 2014

Related U.S. Application Data

(60) Provisional application No. 61/793,037, filed on Mar. 15, 2013.

(51) Int. Cl.
| | |
|---|---|
| *G01N 33/569* | (2006.01) |
| *G01N 33/50* | (2006.01) |
| *G01N 33/543* | (2006.01) |
| *B01L 3/00* | (2006.01) |

(52) U.S. Cl.
CPC ........ *G01N 33/56972* (2013.01); *B01L 3/5023* (2013.01); *G01N 33/5047* (2013.01); *G01N 33/54313* (2013.01); *B01L 2200/04* (2013.01); *B01L 2300/0825* (2013.01); *G01N 2333/70514* (2013.01); *G01N 2333/70517* (2013.01)

(58) Field of Classification Search
CPC ............... G01N 33/56972; G01N 33/5047; G01N 33/54313; B01L 3/5023
See application file for complete search history.

(56) References Cited

U.S. PATENT DOCUMENTS

| | | | |
|---|---|---|---|
| 5,122,453 A | 6/1992 | Martin | |
| 6,045,694 A * | 4/2000 | Wang et al. | 210/500.37 |
| 6,713,298 B2 | 3/2004 | McDevitt | |
| 6,743,591 B1 * | 6/2004 | Okubo et al. | 435/7.1 |
| 8,377,398 B2 * | 2/2013 | McDevitt et al. | 422/554 |
| 2008/0050830 A1 | 2/2008 | Floriano | |

* cited by examiner

*Primary Examiner* — Gail R Gabel
(74) *Attorney, Agent, or Firm* — Boris Leschinsky

(57) ABSTRACT

A method for quantitatively measuring white blood cell (leukocyte) count and/or white blood cell (leukocyte) subsets count involves adding specific antibodies labeled with a marker to the biological fluid sample, capture of white blood cells from a fluid sample by a retainer, removal of other than leukocyte cells and other interfering substances by washing or using specific magnetic beads, and reading the result. The device for use in the present method includes a retainer for leukocyte cells and an absorption pad for taking up all excess washing solution flowing past the sample.

17 Claims, 8 Drawing Sheets

FLOW-THROUGH CELL COUNTING ASSAY

GOVERNMENT SUPPORT

The present invention was made with a US Government support under SBIR Grant No. 1 R43 HL097933 entitled "A FLOW-THROUGH CELL COUNTING ASSAY" awarded by the National Institutes of Health, National Heart Lung and Blood Institute. The government has certain rights in this invention.

BACKGROUND

The present invention relates to methods and devices for determination of a leukocyte count and/or leukocyte subset count in biological fluids.

The tests for white blood cell, WBC (leukocyte) count and leukocyte subsets count are widely used in clinical practice. In general, laboratory methods for quantification of WBC or WBC subsets are based on the use of automated cell counting instruments and require 3-5 mL of venous blood samples, which are first diluted and then cells of different sizes and shapes are counted in a flow chamber[1]. Instruments which are utilized for automated cell counting are complex and costly, and only available in very few central hospitals and other larger laboratories. In addition, they require professionally trained personnel to operate the instruments.

At present, there is an increasing demand to reduce the turnaround time of test results, and new point-of-care testing (POCT) technologies are being developed for rapid diagnosis at or near patients' bedside. POCT devices are portable and user-friendly to operate, and, therefore, are of great value in both developing and developed countries, where access to automated cell counters is restricted, for instance in rural clinics or general practices.

Rapid measurements of leukocyte and their subsets are important in many clinical situations. They can be useful when physicians need to make decisions regarding the initiation (or monitoring) of treatment when the patient is still at clinical setting. The ability of POCT to provide results within minutes allows physicians to do it and use the results right away.

In hematology testing, there are three types of technology to support POCT: small bench-top analyzers, hand-held devices and manual tests. The bench-top systems are often smaller versions of laboratory analyzers, providing a full blood count (FBC) with red cell indices and either a five-part white cell differential or a partial three-part differential. Bench-top analyzers, however, are not useful at the patient's bedside and are not truly POCT devices because they are designed for use in clinics or small laboratories. The hand-held test devices and manual methods include measurement of hemoglobin (Hb) concentration, WBC and platelet count, detection of malaria and enumeration of CD4+ T-lymphocytes for human-immunodeficiency-virus (HIV) diagnosis and treatment monitoring[2; 3; 4].

Clinicians routinely use WBC and differentials (subsets) as biomarkers for acute infection/inflammation in various clinical settings from primary to critical care. An increased WBC count occurs in infection, allergy, systemic illness, inflammation, tissue injury, and leukemia. A low WBC count may occur in viral infections, immunodeficiency states, post chemotherapy, acute leukemia. For example, patients who are on chemotherapy need to check their WBC count frequently to ensure that they are eligible for the next treatment.

An increased or decreased total white blood cell count (WBC) could be due to abnormal bone marrow pathology[5]. Leukocytosis with an associated neutrophilia or lymphocytosis could infer the presence of a microbial or viral infection[3]. Leukocytosis is also a prognostic marker of patients who are at a higher risk of hospital mortality[6; 7] and identifies patients at increased risk for excessive bleeding[8]. Thus, clinicians can use the WBC biomarker to improve risk prognostication and identify patients in need of immediate treatment and a closer follow-up[9].

At present, there are several commercially available methods for the WBC count that can be used as POCT tests: 1) HemoCue WBC (Angelholm) [10], 2) the Chempaq XBC analyser (Chempaq A/S; Hirsemarken 1B, Farum, Denmark) [11], 3) PortaWBC™ (PortaScience, Moorestown, N.J.), and 4) the traditional procedure for the total and differential WBC count by manual microscopy[12].

The HemoCue WBC device measures total WBC without giving any differential. It consists of a microscopic image detector, a cuvette holder and an LCD display unit. The method is based on drawing peripheral capillary blood or venous blood into a plastic cuvette containing a reagent where the red cells are haemolysed and the nuclei of the white cells stained by methylene blue. Then, an image is captured, and the image analysis program counts WBC.

The Chempaq XBC hematology analyzers comprise a disposable cartridge and an instrument, and use impedance cell counting and measurement of Hb by a spectrophotometric method on 20 µl of blood. Thus, the aforementioned two instruments use rather complex instrumentation.

The PortaWBC™ method for quantitatively measuring white blood cell count involves capture of white blood cells from a fluid sample by a retainer that has a dye substrate immobilized therein, washing, and reading the result of a color reaction in which an ester which is present on the white blood cells cleaves a chromogenic substrate which produces a water insoluble dye. The signal is read using a glucose-like meter which measures the sample reflectance.

The total WBC count is obtained by lysing red blood cells in 2% acetic acid solution and counting WBCs in the hemacytometer chamber. For the differential WBC count, a stained smear is examined under microscope in order to determine the percentage of each type of leukocyte present. Stains for preparing whole blood smears are available from numerous manufacturers. Standard manual cell counting methods are time consuming and subjective. It is a common occurrence to obtain cell counts with wide inconsistencies in total cell counts. Likewise, the traditional procedure for the differential WBC count has a poor statistical reliability. In addition to that, it is time consuming, requires experience to make technically adequate smears consistently, and therefore is one of the most expensive routine tests in the clinical hematology laboratory[13]. Although the latter two methods are simpler and use less expensive equipment than the first two methods, they are labor-intensive and time-consuming. In addition, the PortaWBC™ method does not allow for determination of leukocyte subsets such as neutrophils, eosinophils, basophils, lymphocytes, monocytes, macrophages, dendritic cells, and granulocytes.

Very important parameters which are measured for diagnosis of HIV infection and monitoring of HIV patients are CD4+ T-lymphocyte levels for adults and CD4 percentage for pediatric patients.

HIV infection is one of the major problems in public health. It is estimated that more than 1.1 million HIV-infected persons are living in the United States and roughly 33.3 million people are living with HIV worldwide. In the recent years much importance is being given to a wider HIV screening and identification of infected individuals for implementation of intervention strategies. HIV testing has gained immense therapeutic relevance: starting the highly active antiretroviral therapy (HAART) early may improve quality of life and considerably prolong life. Treatment with HAART has dramatically improved survival rates in HIV since its introduction in 1995.

Individuals with HIV infection and AIDS exhibit abnormalities of the immune system, reflected primarily in their CD4 T lymphocytes, which are targeted by the virus. In adults, the evaluation of CD4 levels provides an important assessment of immunologic competency and has proven to be the most important test for HIV progression. Results from the measurement of CD4 lymphocyte levels provide information that guides therapy and predicts disease outcome. For example, new US guidelines favor antiretroviral therapy for patients at 350-500 CD4 cells/μL. New WHO recommendations are to start HAART for HIV patients with CD4 cell counts at or below 350 cells/μL, instead of a CD4 cell count of 200 cells/μL, the threshold which the WHO recommended in its 2006 guidelines. Normally, T lymphocytes (CD4 and CD8) account for 60-90% of all lymphocytes. Their numbers are about 1,600 cells/μl, with CD4 cells accounting for approximately 1,000 and CD8 cells approximately 500. CD4 cells are the main target of HIV and the number of CD4 cells will gradually decrease during HIV infection (50-100 cells/μl per year). HIV-positive individuals who are successfully treated with HAART demonstrate an increase in the CD4 cell count.

In pediatric patients, the high variability of absolute CD4+ T count occurs within the first 5 years of age. In addition, incurrent illnesses may affect CD4+ counts and the "normal" reference ranges for CD4 T+ cell absolute counts in African children differ from those reported for populations in Europe and North America[14; 15]. Therefore, in pediatric patients aged less than 5 years, it is strongly recommended that percentage of CD4+ T cells is determined within the total lymphocyte population (% CD4/ly)[16; 17]. If available, the percentage of CD4+ T cells is utilized to establish the level of immunodeficiency and make decisions when to start cotrimoxazole (CTX) prophylaxis and/or ART in all HIV infected children less than 5 years of age[18].

Relative to adults, very high absolute lymphocyte counts are seen in neonates (6,500±2,200 (SD) lymphocytes/μL) with a gradual decrease to near adult levels in children greater than 5 years of age (1,900±550 (SD) lymphocytes/μL)[19]. For classification of the HIV-associated immunodeficiency, the following % CD4/ly values are considered: mild immunodeficiency is suggested if % CD4/ly is 30-35% in infants, 25-30% in children aged 12-35 months, and 20-25% in children between 36-59 months of age. Severe immunodeficiency occurs when the % CD4/ly values in the age groups mentioned above drop below 25%, 20%, and 15%, respectively[18] World Health Organization (WHO) recommends initiation of CTX prophylaxis in all HIV-exposed children under the age of 1 year irrespective of their % CD4/ly measurement, particularly, in resource limited settings where infant HIV status may not be established until the age of 18 months due to the lack of proper technology[18]. In settings where % CD4/ly measurements are available, WHO recommends to initiate CTX prophylaxis in the 1-4 year age group if % CD4+/ly is less than 25%. The initiation of ART is determined by clinical presentation of disease and % CD4/ly measurements. ART is indicated for all HIV-infected individuals with an AIDS defining illness[18]. In pediatric patients <5 years of age with non-AIDS defining illness, ART is initiated at severe level of immune deficiency as determined by % CD4/ly[18].

Strategies to Assess Lymphocytes. Lymphocyte subsets are typically measured by immuno-fluorescent labeling of cells with fluorochromes conjugated to specific monoclonal antibodies and quantifying the proportion of specifically labeled cells by flow cytometry. Manual alternatives to flow cytometry are also available to quantify CD4 cells. They are simple light or fluorescence microscopy methods that just require cell counting.

Flow Cytometry. In flow cytometry, specific monoclonal antibodies made against the specific CD antigens present on the cells are labeled with fluorescent dyes. The labeled monoclonals are allowed to react with the mononuclear cells (lymphocytes and monocytes), and the cells that react can be classified by the flow cytometer into subpopulations depending on which monoclonals are bound. Flow cytometry generally gives the percentage of CD4+ or CD8+ cells. To obtain absolute cell counts, dual and single platform technologies are used. A dual platform technology employs a flow cytometer and a hematology analyzer. CD4 absolute count using dual platform approach is a product of three measurements: the white blood cell count, the percentage of white blood cells counts that are lymphocytes (differential), and the percentage of lymphocytes that are CD4 cells (determined by flow cytometry). If a single platform technology is used, absolute counts of lymphocyte subsets are measured in a single tube by a single instrument. Usually it is accomplished by spiking a fixed volume of sample with a known number of fluorescent beads (bead-based systems) or by precisely recording the volume of the sample analyzed. Recent recommendations suggest that single platform technology should be the gold standard for the CD4 absolute count.

Several varieties of flow cytometers are available, with the FACSCalibur (Becton Dickinson) and EPICS XL (Beckman Coulter) being the most popular. These instruments offer high sample throughput, workflow management through automation, and simple software applications. Both instruments can detect four colors and measure relative cell size and cellular complexity. The systems are designed to use whole blood, collected in liquid EDTA. Besides using the traditional flow cytometers (open platforms that can employ dual or single platform technology), the simplified dedicated platforms are developed for CD4+ T-cell counts. The commercially available dedicated platforms include FACScount (Becton Dickinson), CyFLow Counter (Partec), and Guava Auto CD4/CD8% (Millipore/Merck). The dedicated platforms allow CD4+ T-cell counting with reduced technical complexity. It produces absolute CD4 counts and a CD4/CD8 ratio without requiring an external computer. The system uses whole blood, eliminates the need for lysis and wash steps, and has a unique software algorithm that automatically identifies the lymphocyte populations of interests. However, the instrument costs about $25,000, with each assay costing $3-20 depending on volume of tests performed in the laboratory.

Flow cytometry, even though the "gold standard" reference method for determining lymphocyte subpopulations, has several disadvantages: the method requires an expensive instrument ($25,000-90,000), an expensive service contract, and well-trained personnel. Highly trained personnel and costly equipment make it difficult for small laboratories or those in developing countries to routinely provide this testing.

Manual Methods to Quantify Lymphocytes. Manual alternatives to flow cytometry available on the market are: the Cyto-Spheres (Coulter Corporation, USA) and the Dynabeads (Dynal AS, Norway). The Dynal T4 kit (the Dynabeads) is used to manually count CD4 cells in a cell counting chamber under a microscope. This method measures CD4 absolute count; no lymphocyte percentages can be determined. It requires an epifluorescent microscope (recommended), although it can be performed with only a light microscope; a hemacytometer, a vortex, a tube rocker, a timer, and a magnet. Magnetic beads are coated with monoclonal antibodies as a solid phase to isolate CD4 and CD8 cells from whole blood, whereas CD4-positive monocytes are pre-depleted using CD14 magnetic beads. After isolation of CD4 cells, the cells are lysed, stained, and counted. Blood samples should be fresh, preferably not older than 24 hours. The Coulter Manual CD4 Count Kit (cytospheres method) requires a light microscope, timer, and a hemacytometer and measures CD4 absolute counts (no percentages) from whole blood collected in EDTA tubes [20]. Antibody-coated latex particles are used to bind CD4 cells resulting in a "rosette" of latex beads around each CD4 cell; the rosette is readily recognized by light microscopy. A monocyte blocking reagent minimizes the interference from monocytes that contain CD4 antigens because they can be recognized during CD4 cell counting. Blood should be tested within 6 hours of collection and should not be refrigerated. Both manual assays cost between $5-6 per test and are designed to operate with low sample throughput in resource-limited laboratories. However, the manual methods are labor-intensive; require many manual steps, and an experienced microscopist. Large intra- and inter-operator variations are the norm rather than the exception and these methods have been proven very difficult to implement in most settings.

New CD4 Technologies. Recent development of CD4 technologies is concentrated on creating an accurate point-of-care (POC) assay that could be used for CD4 testing in resource-limited countries in any health care setting or in the field. Inverness Medical (now Alere) has a PIMA CD4 test based on static image analysis and counting principles. A disposable cartridge containing dried reagents and a portable analyzer is used. The analyzer is easy to operate: no extensive training is required. The cost of analyzer is $5,500; an estimated cost per test is $6. The assay is already available in select markets. Daktari Diagnostics is developing a microfluidic-based system to capture CD4 cells and to count cells using simple electrical impedance measured by a small portable device. The estimated device cost is $800 and the single test cost is estimated to be $8. mBio Diagnostics, a division of the Precision Photonics Corporation has a new patent-protected CD4 count technology that uses an integrated fluidic cartridge and a portable fluorescence imaging device. Zyomyx is another company involved in the development of a POC CD4 test: Zyomyx CD4 counter is similar to a thermometer where CD4 cell stacking height highly correlates with CD4 count in the blood sample. The major advantage of this assay is that it does not require any instrument for reading the results. The estimated cost of the assay is $6-7, however, this assay is still under development. A different new CD4 technology developed by Burnet Institute in Australia is based on the measurement of CD4 protein on T-cells, rather than measuring CD4 cells using a lateral flow assay. The test, which is expected to cost about $2, is semi-quantitative: it will be able to determine, whether a patient's CD4 count is above or below a threshold of 350 CD4 cells/µL, but it will not give full quantitative results. The reader of the test is expected to cost about $1,200. The above mentioned POC tests are promising, however, they still need to be evaluated in the clinical trials: peer reviewed published data is available only for PIMA CD4 test. All other tests still need to stand up to robust assessment.

Current flow cytometric methods to measure CD4 cells are expensive, require significant technical expertise, the instrumentation has high service demands, and these methods are difficult to support in resource-limited countries. The aforementioned manual CD4 tests have their advantages and limitations. Indeed, Dynabeads (Dynal Biosciences) and Cytospheres (Coulter), methods are multi-step assays and require a microscope for counting targeted cells, what leads to increasing of the assay cost. In addition, these manual methods are laboratory-based and their procedures are not conducive for point-of-care workers such as nurses, counselors, and physicians. Moreover, currently there are no manual methods on the market that provide % CD4/ly measurement. Thus, the rationale is to develop and validate a truly point-of-care CD4 method that can be used by non-laboratory personnel in a wide variety of health care settings and in the field to provide anti-retroviral treatment decisions immediately and without the need for infected persons to return for results. Serious limitations of the aforementioned methods hinder their wide use in clinical practice. Therefore, the development of an alternative manual assay that is free from the above drawbacks is of utmost relevance.

SUMMARY

It is an object of the present invention to overcome limitations of the methods cited above.

It is another object of the present invention to provide a method for quantification of white blood cell (leukocyte) and their subsets count in a biological fluid.

It is another object of the present invention to provide a device for estimating WBC and their subsets count in a biological fluid.

The method of the present invention, the flow-through cell counting assay (FTCA), employs a special filter that selectively captures white blood cells (WBC) and a flow-through cassette to measure cell count status.

The methods of the present invention in general include the following steps: a) adding to biological fluid sample of an antibody specific to total leukocyte or to at least one leukocyte subset, this antibody is conjugated with a marker; b) incubating the biological fluid sample for duration from about 5 min to about 60 min and at a temperature ranging from about 20 degrees Celsius to about 37 degrees Celsius; c) filtering the biological fluid sample through a retainer filter to bind the leukocytes of the biological fluid sample onto the retainer filter; d) washing the retainer filter to remove weakly-bound substances; and e) reading the marker for determining of the total leukocyte or at least one leukocyte subset in said biological fluid.

In embodiments, another variant of the assay may be based on the selective adsorption of white blood cells by the retainer filter. In this version of the test, however, magnetic beads carrying specific antibodies against interfering substances may be added to the biological fluid and after incubation may be removed before filtering the biological fluid through retained filter.

The device of the present invention may include a cartridge comprising a cartridge housing supporting a fluid sample acceptance tube, an absorbent pad, a removable strip containing a retainer filter configured for binding of leukocytes of biological fluid sample.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION OF THE INVENTION

Figure 1:
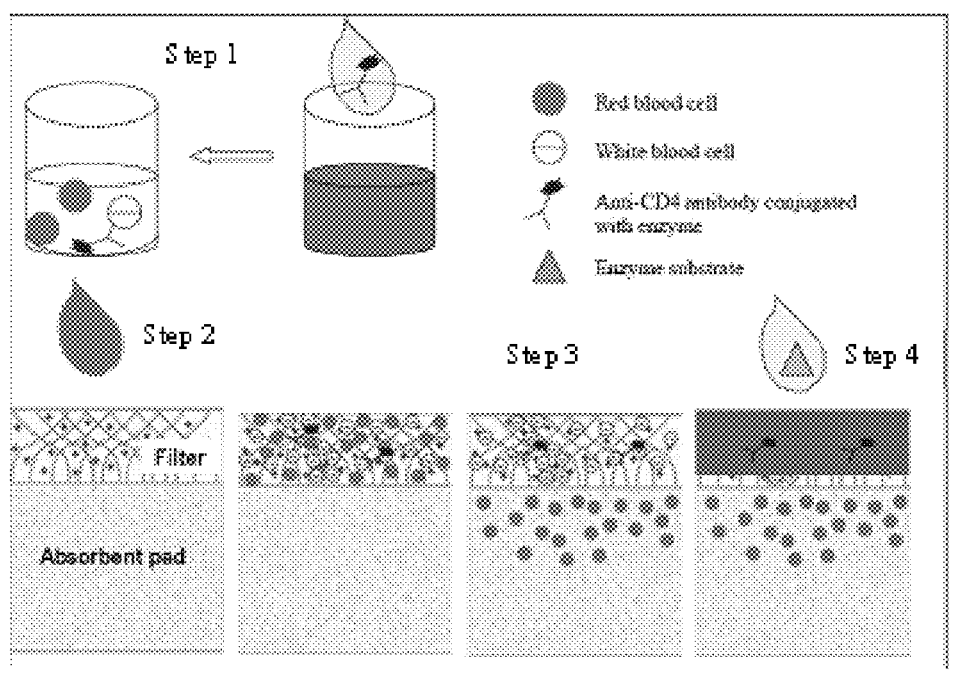
FIG. 1 shows a block-diagram of conducting FTCA for enumeration of CD4+ T-lymphocytes cells.

The following description sets forth various examples along with specific details to provide a thorough understanding of claimed subject matter. It will be understood by those skilled in the art, however that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

The method of the present invention may be used for enumeration of the total leukocyte and/or at least one leukocyte subset such as for example neutrophils, eosinophils, basophils, lymphocytes, monocytes, macrophages, dendritic cells, granulocytes, and their respective subsets as well as one or more ratios of one desired subset count to another desired subset count.

The method is further described as it applies to determination of specific WBC subset count, which is meant only to be illustrative of the method and not to limit the scope of the claims that follow. One skilled in the art would recognize the utility of the present invention in other WBC subset count assays utilizing this method. The description of some other such assays is also provided.

For example, FIG. 1 shows one of the general approaches of conducting FTCA for enumeration of CD4+ T-lymphocytes cells. This variant of assay comprises the following steps: 1) An anti-CD4 antibody conjugated with enzyme may be added to whole blood; 2) After several minutes of incubation, the sample may be delivered to the flow-through cassette. The cassette may comprise a retainer filter and an absorbent pad. The retainer filter may be configured to selectively retain white blood cells, including CD4 antibody-T-cell complexes; 3) A washing buffer solution may be poured through the cassette to remove substances from the sample unbound (or weakly bound) by the retainer, such as for example red blood cells, enzymes, enzyme inhibitors, proteins, and lipids; 4) Then, an enzyme substrate may be added, and the result of a color-forming reaction of the enzyme with an insoluble chromogenic substrate may be read either by eye or by an instrument.

In order to determine other than CD4+ T-cell subset of WBC, specific antibodies to the particular WBC subset may be used. For instance, anti-CD8 antibody may be used for determining of CD8+ T-cell lymphocytes; and anti-CD45 antibody (or other antibodies such as anti-CD52, CD 81, CD96, CDw137, CD200 antibodies) may be used for determining of total leukocytes or total lymphocytes.

The methods of the present invention may be based on the use of filters that selectively capture white blood cells whereas other potentially interfering weakly-bound to the filter substances such as red blood cells, enzymes, enzyme inhibitors, proteins, and lipids can be removed by washing. The selective capturing of white blood cells onto the filter occurs because white blood cells (leukocytes) are negatively charged, whereas the retainer filter has a net positive charge. Filters that selectively bind WBC are known to be used for filtering white blood cells from blood intended for transfusions. These filters can capture 30-80% of the white blood cells from whole blood due to their well-controlled surface charge and pore sizes. Commercially available filters used for leukocyte reduction apply selective filtration technology combining depth and adsorption filtration to achieve the highest efficiency. The features of filters for leukocyte reduction also include high leukocyte absorption rate and ease-of-use. Depth filters are usually composed of densely packed fibers to remove particles, either by adherence or absorption onto the fibers, or by entrapment between fibers as particles pass through the filter. Adsorption filters utilize the properties of white blood cells, which selectively adhere to filter fibers.

Several types of the filters (membranes) may be used for the methods of the present invention:
 a. Leukosorb type filters from Pall Life Sciences, the surface characteristics of which was grafted by compounds containing an ethylenically unsaturated group, such as an acrylic moiety combined with a hydroxyl group. Monomers such as HEMA or acrylic acid are used;
 b. Certain grades of cellulose paper that possess positively charged surfaces;
 c. 3 μm Nuclepore polycarbonate, track-etch filters (Whatman, Florham Park, N.J. and Sterlitech Corp., Kent, Wash.). These membranes selectively capture lymphocytes and provide for the removal of red blood cells without sample processing because the more rigid leukocytes are retained by the porous membrane while the more flexible erythrocytes, as well as plasma are relegated to waste; and
 d. Sepacell R-500 (Asahi Medical Co Ltd, Tokyo, Japan).

Although some of the aforementioned filters may be used successfully for detection of some WBC subsets such as total WBC count, they may not be suitable for detection of some of the WBC subsets such as CD4+ T-cell lymphocytes, CD8+ lymphocytes, and total lymphocytes. The reason for this is that different WBC subsets may carry the same antigen, and, therefore, the use of a one set of antibodies to this antigen may lead to detection of not only the targeted cells but, also, to detection of potentially interfering cells.

For example, one of the main problems of all manual tests for CD4+ T-lymphocyte cells is the interference of monocytes. In embodiments, an anti-CD4 antibody conjugated with a marker may be used for determination of CD4+ T-lymphocytes. However, monocytes as well as CD4+ T-cells carry CD4 antigens (although about 10 times less), and anti-CD4 antibodies used for enumeration of CD4 antigens may bind to monocytes, which results in erroneous increase in CD4 count. Therefore, in most CD4 manual tests using anti-CD4 antibody, monocytes may be first removed from blood, and then CD4 cells may be counted. The additional step of monocyte removal obviously complicates the test procedure.

In embodiments, CD4 percentage, that is the ratio of CD4+ T-cell count to total lymphocyte count, may be calculated. In this case, both CD4+ T-cell and total lymphocyte counts have to be determined. In the method of the present invention, anti-CD45 antibody may be used for determination of the total lymphocyte count. However, not only lymphocytes but also other WBC subsets such as neutrophiles (granulocytes) and monocytes contain CD45 antigen.

Thus, in order for the membrane filter to be suitable for FTCA, it needed to possess the following three main properties:
a. ability to selectively capture as many white blood cells (WBC) as possible,
b. ability to allow cells other than WBC blood cells to be washed out; and
c. the ratio of captured (adsorbed) lymphocytes to monocytes and granulocytes needs to be as high as possible in the case when CD4+ T-lymphocytes and total lymphocytes are detected. In particular, the amount of lymphocytes captured on the filter needs to be sufficient to register the signal obtained using anti-CD4 or anti-CD45 detection reagents. This signal also needs to be specific in order to avoid detection of other types of CD4+ or CD45+ carrying cells, such as granulocytes and monocytes.

Examples of commercially available leukocyte-reduction filters, which provide the highest ratio of adsorbed lymphocytes to monocytes, and gave the best results for enumeration of CD4+ T-cells in whole blood (see results below) include LRF10S filter (Pall Inc., Long Island, N.Y.). This retainer filter is configured for capturing leukocytes in such a way that the captured leukocytes retained on said preferential retainer filter consist of approximately 80 percent or more of the lymphocytes and approximately 20 percent or less of any other subset of the leukocytes.

Still in another aspect of the invention, the potentially interfering cells may be removed by adding magnetic beads carrying at least one antibody selected to bind to at least one interfering substance to biological fluid sample; incubating the sample for a certain period of time; and removing magnetic beads together with at least one interfering substance from biological fluid sample using a magnet. Still in another aspect of the invention, the potential interference of other than targeted cells may be diminished by using more specific antibodies to the targeted cell. For example, in the method of the present invention, other than anti-CD45 antibody such as but not limited to anti-CD52 antibody, anti-CD81 antibody, anti-CD96 antibody, anti-CDw137 antibody, and anti-CD200 antibody may be used for determination of the total lymphocyte count.

The antibody markers of different origins may be used for the methods of the present invention such as for example: a) an enzyme, b) an enzyme complex, c) a plurality of gold microparticles, d) a plurality of quantum dot microparticles, e) a plurality of fluorescent latex microparticles, f) a plurality of fluorescent liposomes, g) a fluorescent dye, h) a photochemical dye, i) an chemiluminescent compound, and j) an electrochemiluminescent compound.

In another aspect of the invention, the marker is a biotin and a streptavidin conjugate or an avidin conjugate of a material selected from a group consisting of an enzyme, an enzyme complex, a plurality of gold microparticles, a plurality of quantum dot microparticles, a plurality of fluorescent latex microparticles, a plurality of fluorescent liposomes, a fluorescent dye, a photochemical dye, a chemiluminescent compound, and a electrochemiluminescent compound.

In yet another embodiment of the invention, the marker may be an Alkaline Phosphatase (AP) or a complex of biotin and streptavidin- or avidin-Alkaline Phosphatase conjugate. In this case, before reading the signal, an Alkaline Phosphatase substrate solution may be added. The AP substrate may be of different origins as well, such as for example: a) a chromogenic substrate, b) a fluorogenic substrate, c) a chemiluminescent substrate, and d) an electrochemiluminescent substrate.

A chromogenic substrate may be selected from a group consisting of 5-Bromo-4-chloro-3-indolyl phosphate/p-iodonitrotetrazolium (BCIP/INT); 6-chloro-3-indoxyl phosphate, p-toluidine/NBT (BCIP pink/NBT); 3-indoxyl phosphate/NBT; Fast Red TR/Naphthol AS-MX phosphate; Fast Red TR/Naphthol AS-TR phosphate; and p-nitrophenol phosphate (pNPP).

A fluorogenic substrate may be selected from a group consisting of 4-methylumbelliferyl phosphate (4-MUP); 6,8-Difluoro-4-methylumbelliferyl phosphate (DiFMUP); Fluorescein diphosphate (FDDP); 2'-[2-benzthiazoyl]-6'-hydroxy-benzthiazole (BBTP); 2-(5'-chloro-2-phosphoryloxyphenyl)-6-chloro-4(3H)-quinazolinone (ELF 97); Acridinium (N-sulfonyl) carboxamide and acridinium ester-based substrates; and Rhodamine 110-based phosphates.

A chemiluminescent substrate may be selected from a group consisting of Acridinium (N-sulfonyl) carboxamide and acridinium ester-based substrates; 1,2 Dioxetane-based substrates (4-methoxy-4-(3-phosphatephenyl)spiro[1,2-dioxetane-3,2'-adamantane]; and disodium salt-based substrates (AMPPD).

An electrochemiluminescenct substrate may be a ruthenium salt-based substrate.

The marker may be detected visually by eye or by using an optical instrument or by using an electrochemical instrument. Indeed, if the enzyme and a chromogenic insoluble substrate or chromogenic gold or colored latex particles are used as markers, the signal may be detected either by eye or by a reflectometer. If the enzyme chromogenic soluble substrate is used, a photometer (optical density reader) may be used. If fluorescent materials such as fluorochromes, dyes, fluorescent latex particles are used as markers and enzyme fluorescent substrates are used, then a fluorimeter may be utilized for reading the signal. When a chemiluminescent signal is generated, a chemiluminometer may be used for signal detection. Electrochemical detection may also be possible when an electrochemical signal is generated using enzyme substrate and registered by using a reader of electrical parameters.

The methods of the present invention may be used for determination of WBC and their subset counts in biological fluid samples such as whole blood, a blood fraction, a cerebrospinal fluid, urine, saliva, and perspiration.

Construction of the Flow-Through Cell-Counting Assay Cartridge

Figure 2:
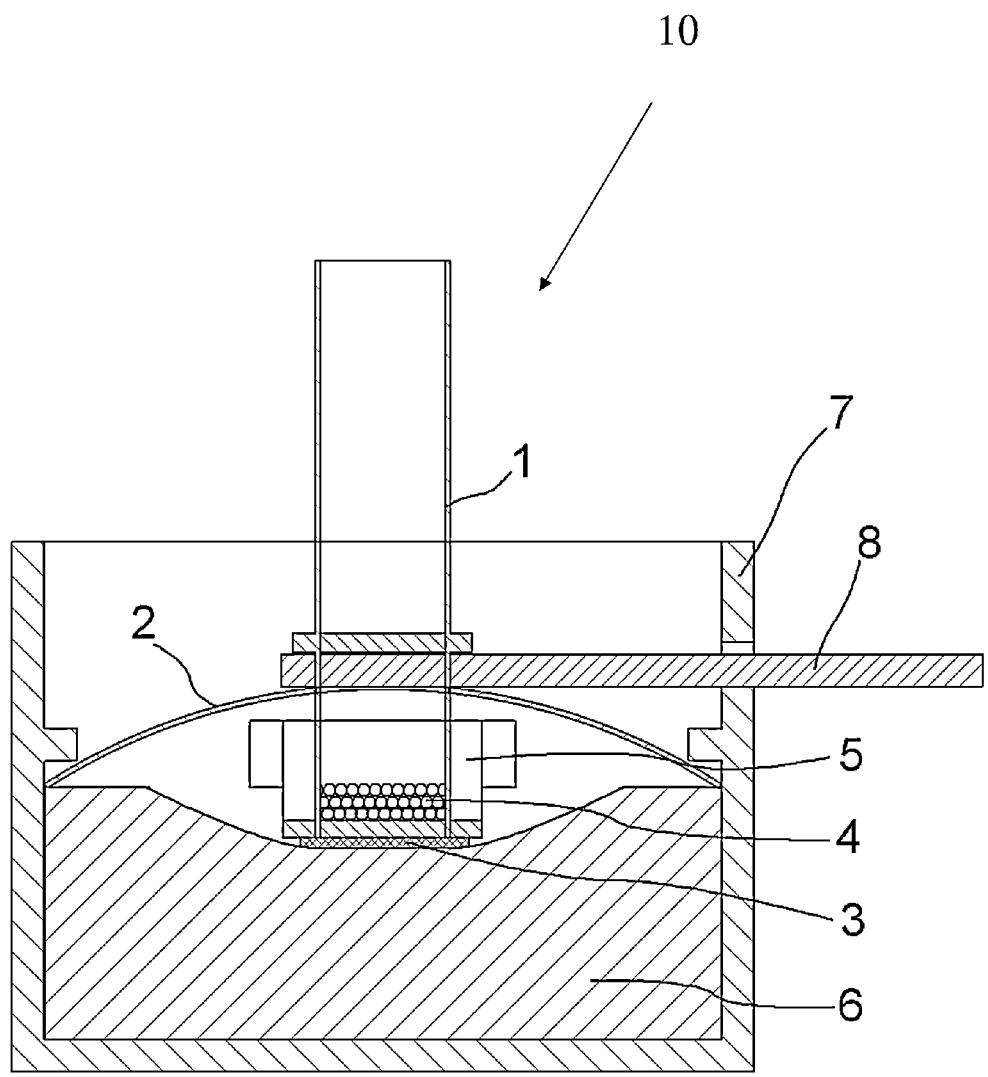
FIG. 2 shows a front cross-section view of the device of the present invention.
Figure 3:
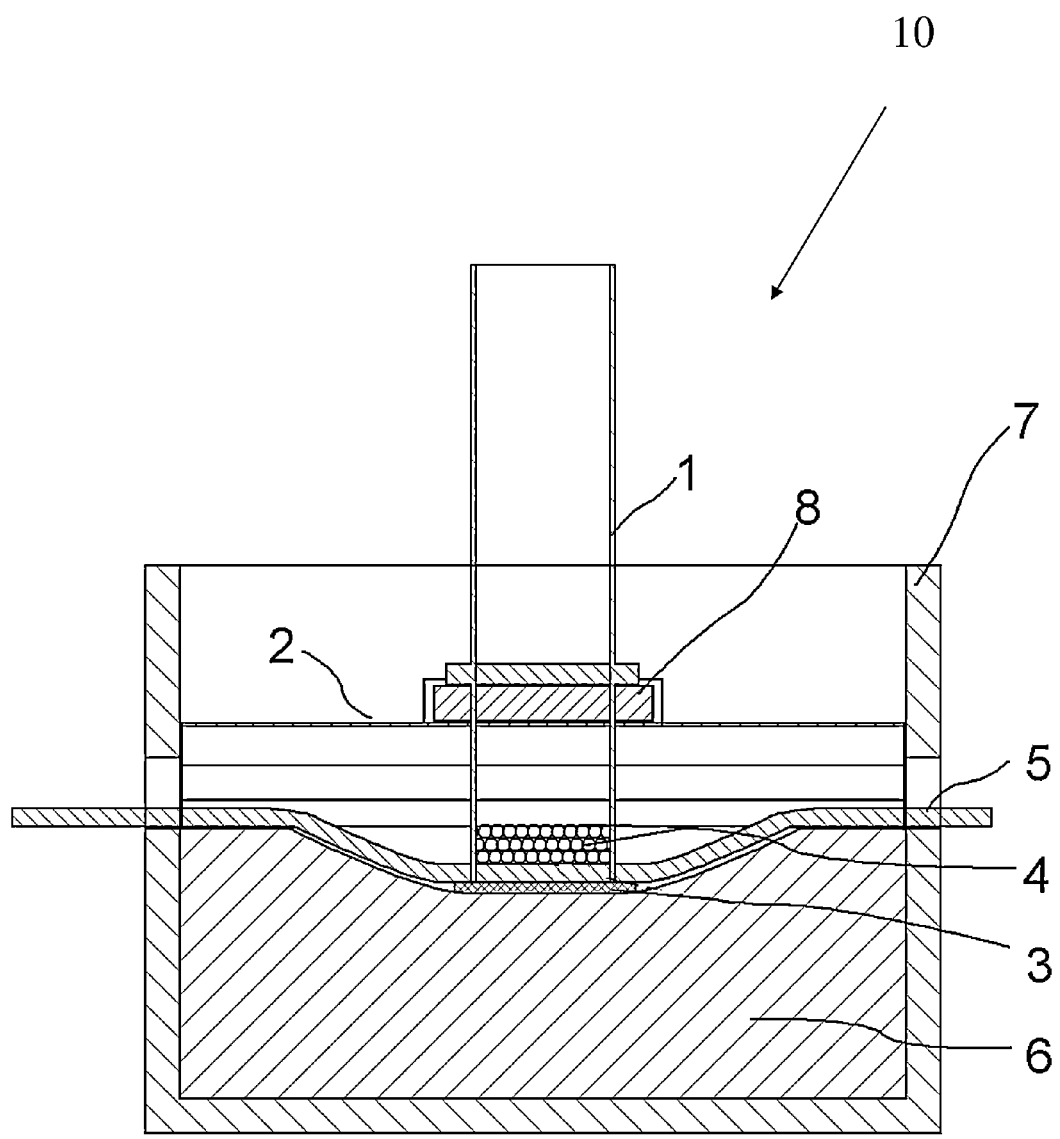
FIG. 3 shows a side cross-section view of the device of the present invention.
Figure 4:
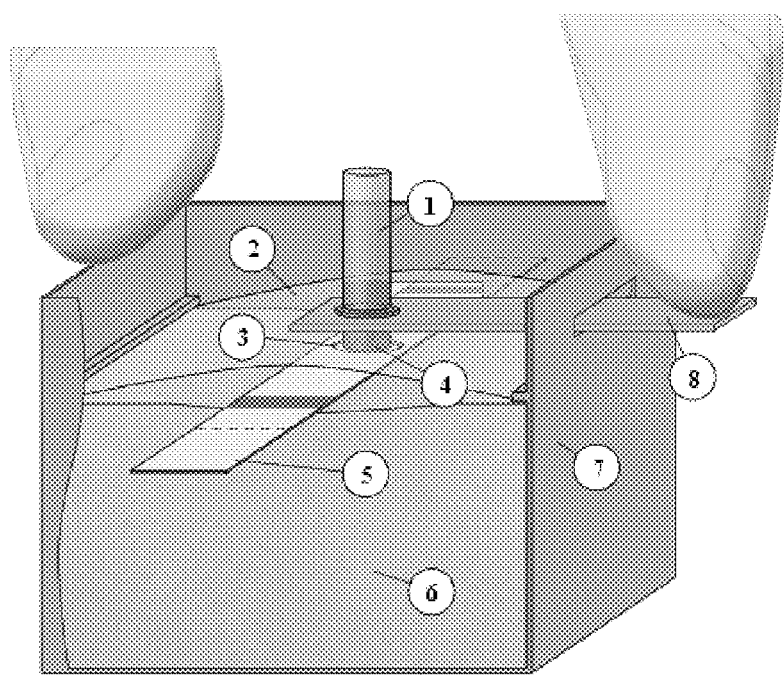
FIG. 4 illustrates a general view of the device of the present invention.

The general concept of a disposable cartridge design and manipulation technique for whole blood testing are illustrated in FIG. 2 (front cross-section view), FIG. 3 (side cross-section view) and FIG. 4 (general view). The main idea of the FTCA cartridge is that a strip can be inserted into the cartridge, and pulled out from the cartridge for subsequent optical detection analysis. The cartridge generally comprises a cartridge housing supporting a fluid sample acceptance tube, an absorbent pad, a removable strip containing a preferential retainer filter configured for binding of leukocytes thereto and a disengaging mechanism. The preferential retaining filter may be placed between the fluid sample acceptance tube and the absorbent pad and may be configured to retain at least 80 percent or more of the lymphocytes and not more than 20 percent or less of any other subsets of the leukocytes. The disengaging mechanism may be configured to lift the fluid sample acceptance tube from the retaining filter to release the latter for subsequent removal from the cartridge housing using the removable strip.

Discussing the design now in greater detail, the cartridge 10 may contain a string disengagement mechanism (comprising a spring 2 and the lever 8) and an absorbent pad 6 enclosed in a plastic cartridge housing 7. The FTCA cartridge 10 further contains a side slot for inserting and pulling out a removable strip 5 equipped with a retaining filter 3. The removable strip 5 is normally kept in place by the spring 2 pushing down the fluid sample acceptance tube and binding the strip 5 against the absorbent pad 6. The plastic lever 8 plays a role of a leverage. It may be placed through the slot at the side panel of the cartridge housing 7 and attached (glued) to the upper part of the string disengagement mechanism (spring 2) to interact with the lower end of the fluid sample acceptance tube 1. Pushing down on the external end of the lever 8 causes the other end to lift up the spring 2 along with the tube 1 thereby releasing the removable strip 5. Lifting of the string disengagement mechanism 2 may be carried out by holding the cartridge housing 7 down while pressing the lever 8 down as shown in FIG. 4.

In embodiments, a commercially available disposable pipette may be used to collect the exact desired volume of blood (up to 40 μl). After performing a finger stick, blood sample may be taken by the pipette. The blood may then be squeezed out of the pipette into the plastic fluid sample acceptance tube 1.

In embodiments, the fluid sample acceptance tube 1 may contain either a solution or lyophilized anti-CD4 AP-antibody conjugate or a mixture of anti-CD4-biotinilated antibody and streptavidin-AP conjugate (position 4 in FIGS. 2 through 4). After incubation for several minutes, the mixture may be poured into the fluid sample acceptance tube 1 of the FTCA cartridge by pipette, and may go through the preferential retainer filter 3 of the removable strip 5. After washing and adding the substrate solution (and stop reagent, if necessary), the removable strip 5 may be pulled out and analyzed by a blood glucose-type meter (reflectometer) or by eye using a reference color chart.

In alternate embodiments, the surface of the removable strip 5 may be made very smooth and may be coated with a hydrophobic polymer material, for example by silane or ethylcellulose derivatives[21] except, of course, the round area containing the retainer filter 3 (FIGS. 2, 3, 4). This may be done for the following reason: in the initial position of the removable strip 5 inside the cartridge 10, the fluid sample acceptance tube 1 may touch the removable strip 5 not in the area where the retainer filter 3 is placed, but in the area which is several millimeter farther to the end of the strip (FIG. 4, dashed line on the strip). This area may contain lyophilized anti-CD4 AP-antibody conjugate 4 (or mixture of anti-CD4-biotinylated antibody and streptavidin-AP conjugate), sprinkled (positioned) through the plastic cylinder during FTCA cartridge manufacturing. As mentioned above, whole blood may be poured into the plastic cylinder of the FTCA cartridge directly. In order for the blood to stay and not to leak through the bottom of the fluid sample acceptance tube 1 (since several minutes of incubation reagents may be required), the strip surface must be hydrophobic. After incubation, the strip may be pulled out for several millimeters up to the strip broad gray line (FIG. 4). In this case, the removable strip 5 may be released as the fluid sample acceptance tube 1 may be lifted above the preferential retainer filter 3.

In further embodiments, after whole blood is poured through the fluid sample acceptance tube 1, all reagents including anti-CD4 conjugates, wash and stop solutions may be added sequentially. This may be feasible, however, only in the case when high affinity CD4 antibodies are used. Indeed, in this version of the assay, the incubation time may be very short (it equals to the passing time of the solution through the filter), and very high affinity antibodies may be used for the antibody-antigen reaction to occur.

In embodiments, after washing and adding the stop reagent, the removable strip 5 may be pulled out and analyzed in the same manner as described above, that is by blood glucose-type meter or by eye. If a spectrophotometer is available, the removable strip 5 may be placed into the test tube (or cuvette) containing alkaline phosphatase substrate solution in a way that the retainer filter 3 may be completely covered by the substrate solution, and after incubation, the optical density of the sample may be measured.

Quantitative Objective Assessment of Results by Optical Detection

In a further embodiment of the FTCA, the retainer filter 3 of certain diameter may be made integral or attached to the disposable removable paper strip 5. One of the unique features of the FTCA methods is that they allow using several modes of signal detection. For example, the signal may be detected using the following optical methods: 1) visual reading using a chart of colored spots; 2) detection of light reflectance using an inexpensive meter—similar to that used for blood glucose measurement; and 3) detection of optical density of the samples using spectrophotometric methods. The option of using different modes of detection provides flexibility for clinical practitioners in different settings. Indeed, the chart of colored spots and inexpensive optical reader may be successfully used in the field conditions, whereas spectrophotometric method may be used in clinical laboratories. Advantageously, very simple and inexpensive battery-operated spectrophotometers for use in field conditions are readily available. They also may be used for the purposes of the present invention.

Although the described below methods pertain to determination of CD4+ T-cell count, readily understood modifications may be apparent to those skilled in the art allowing adapting the present invention for such purposes as determination of WBC count, total lymphocytes count, CD8+ lymphocytes count and others. The following non-limiting examples for determination of CD4+ T-lymphocytes, total lymphocytes count, and % CD4/ly further illustrate the principles behind the present invention.

EXAMPLE 1

Determination of CD4+ T-Lymphocyte Count for People Greater than 5 Years of Age

In order to be able to determine CD4+ T lymphocyte count in clinical samples of patients older than five years old, the calibration (or standard) curve must be prepared. The targeted clinically significant count range for people older than five years old is between 200 and 1000 cells/μL. For the preparation of the FTCA calibration curve, real fresh whole blood samples from three healthy donors were used. Since all of these samples contain normal levels of CD4 T-cells, samples containing decreased levels of CD4 T-cells were prepared by other means as described below.

Whole blood samples containing decreased CD4 T-cells concentrations may be prepared by depletion of CD3+ cells or CD4+ cells. Since CD4+ depletion leads to reduction of both CD4+ lymphocytes and monocytes, depletion of CD3+ cells was used to keep monocyte concentration in blood samples unchanged. Whole blood samples with reduced CD4 count were obtained by using magnetic beads coated with anti-CD3 antibodies (Dynabeads® CD3) as described in manufacturer's instructions. The final CD4 count in these samples was determined using the manual Dynal® T4 Quant Kit.

Figure 5:
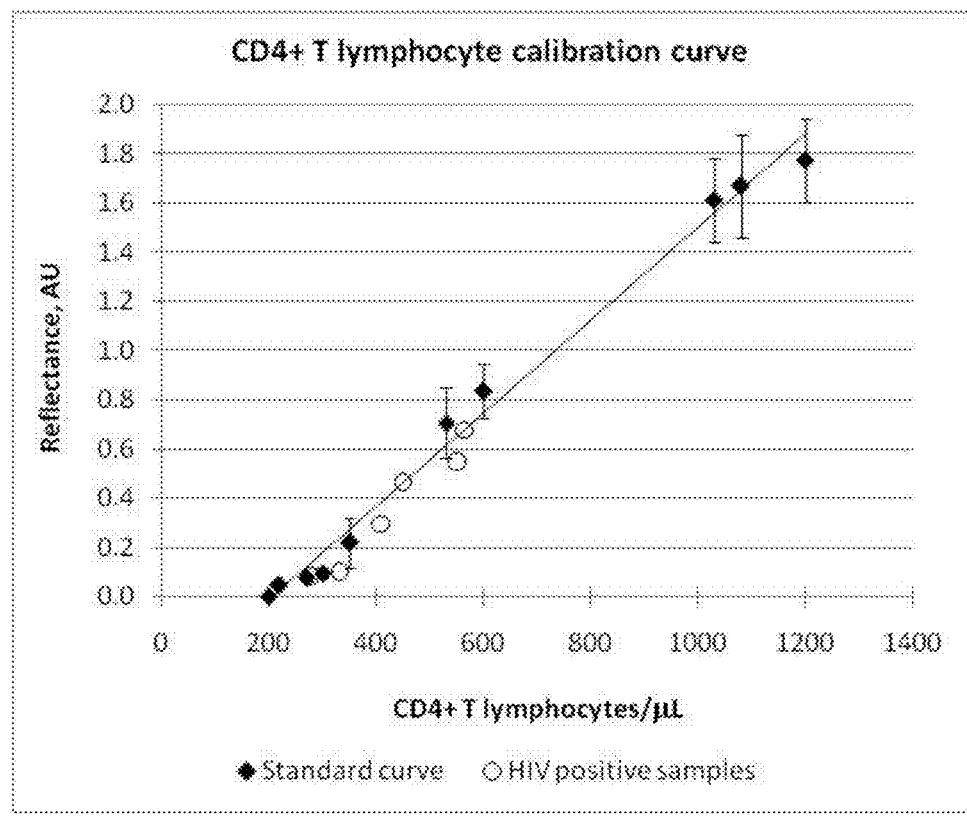
FIG. 5 shows the FTCA calibration curve for determination of CD4+ T-cell count for patients greater than five years of age and HIV positive samples with low CD4 counts.

The following protocol 1 was used: Undiluted anti-CD4 antibody was premixed at 2:1 with Streptavidin-AP (Sigma, Saint Louis, Mo.) diluted in TRIS-buffered saline (TBS, pH 7.4) buffer to the concentration of 24 μg/mL and incubated at room temperature for 30 min. Seventy microliters of WBC-enriched blood, Whole blood or CD3-depleted blood was incubated with 30 μL Strep-AP/anti-CD4 "conjugate" (anti-CD4 and Strep-AP premix) and the samples were incubated for 20 min at RT. Thirty microliters of each sample were placed with a pipette onto the LRF10S membrane incorporated into the flow-through device. After each addition of a sample, 500 μL of wash solution (10 mM TRIS (pH 7.4), 50 μg/mL NBT) were placed with a pipette onto the device five times to wash out the red blood cells. One hundred μL of alkaline phosphatase (AP) substrate (Hercules, Calif.) was added. Ten min after adding AP substrate, 200 μL of stop solution (0.1 N $H_2SO_4$) was added onto each of the membranes. Membranes were removed from the flow-through device and the color intensity was read using portable reflectance colorimeter (FIA Biomed, Germany). A plot of the color measurements (reflectance) versus the CD4+ T lymphocyte count obtained using Dynal® T4 quantification method (Invitrogen, Grand Island, N.Y.) in a range of 200 to 1,000 cells/μL is shown in FIG. 5. This plot may be used as the FTCA calibration curve. As seen in FIG. 5, the calibration curve is linear in the entire clinically significant range of CD4 T-cells concentrations. The most important feature of the FTCA calibration curve is that it allows one to accurately measure signals in the region of CD4 T-cell counts equal to 350 cells/μL the cut-off CD4 concentration used for making a decision as to whether or not initiate an antiretroviral treatment (ART) for HIV positive patients. FIG. 5 also shows that the error of the measurements (coefficient of variation, CV) did not exceed 20% which is acceptable for this kind of assays[22; 23].

As mentioned above, CD4+ monocytes may interfere with the enumeration of CD4+ T-cells if not removed from whole blood before testing for CD4 count. In order to prove that the presence of monocytes in whole blood at high concentrations does not affect the performance of the FTCA test, the following experiment was conducted. The FTCA calibration curve similar to that shown in FIG. 5 was prepared using whole blood samples diluted in 1) the mixture of red blood cells and plasma (1:1) and 2) Phosphate buffer saline (PBS)+plasma (1:1). Thus, unlike the samples used for the preparation of the calibration curve shown in FIG. 5, which contained decreased amounts of CD4 cells and high initial concentrations of monocytes, the samples prepared by simple dilution in the aforementioned solutions contained decreased amounts of CD4 cells and also decreased amounts of monocytes. The calibration curve was then prepared using these samples and showed that it is practically identical to that shown in FIG. 5. FIG. 5 also demonstrates that signals obtained for HIV positive samples containing decreased CD4 counts and normal monocyte concentration (~400-800 cells/μl), as determined by Flow cytometry (FC), were in accordance with those obtained for the samples used for the preparation of the calibration curve. Thus, the above described experiments show that the presence of CD4 monocytes in whole blood does not affect the performance of the FTCA.

EXAMPLE 2

Determination of CD4+ T-Lymphocyte Percentage for Pediatric Patients

The percentage of CD4+ T-cells within the total lymphocyte population (% CD4/ly) may be calculated by finding the ratio of CD4+ T-cells and total lymphocytes counts and multiplied by 100. These parameters may be determined using corresponding calibration curves, which have to cover the clinically significant concentration range between of about 350 to about 3,500 cells/μL for CD4+ T-cells and about 2,000 to about 9,000 cells/μL for total lymphocytes[17].

The calibration curve for CD4+ T-cells determination was prepared as follows (protocol 2). Undiluted anti-CD4 antibody was premixed at 2:1 with Streptavidin-AP (Sigma, Saint Louis, Mo.) diluted in TRIS-buffered saline (TBS, pH 7.4) buffer to the concentration of 24 μg/mL and incubated at room temperature for 30 min. Fifty microliters of WBC-enriched blood, whole blood or CD3-depleted blood was incubated with 30 μL Strep-AP/anti-CD4 "conjugate" (anti-CD4 and S-AP premix) and the samples were incubated for 20 min at RT. Fifty microliters of each sample was placed with a pipette onto the LRF10S membrane incorporated into a flow-through device. After each addition of sample, 500 μL of wash solution (10 mM TRIS (pH 7.4), 50 μg/mL NBT) was placed with a pipette onto the device five times to wash out the red blood cells. One hundred μL of alkaline phosphatase (AP) substrate (Hercules, Calif.) was added after washing. Five min after adding the AP substrate, 200 μL of stop solution (0.1 N $H_2SO_4$) was added onto each of the membranes. Membranes were removed from the flow-through device and the color intensity was read using a portable reflectance colorimeter (FIA Biomed, Germany) as described in the Example 1. CD4+ T cell counts were obtained using Dynal® T4 quantification method (Invitrogen, Grand Island, N.Y.). A plot of the color measurements (reflectance) versus the CD4+ lymphocyte counts in a range of 324-3,610 is shown in FIG. 6.

The calibration curve for the total lymphocyte determination was prepared using the following protocol 3. Whole blood samples with elevated white blood cell counts were prepared by mixing buffy coat layer with red blood cell (RBC) and plasma mixture at a 1:1 ratio. Whole blood samples with low WBC counts were prepared by mixing red blood cells with plasma at a 1:1 ratio. Samples with various concentrations of lymphocytes were prepared by mixing whole blood with samples containing elevated WBCs with RBC/plasma at a 1:1 mixture ratio. For flow-through assay experiments, the prepared blood samples were diluted in WBC-free serum at a 1:1 ratio. Undiluted anti-CD45 antibody (BD Pharmingen, San Diego, Calif.) was premixed at a 2:1 ratio with Streptavidin-AP (Sigma, Saint Louis, Mo.) diluted in TRIS-buffered saline (TBS, pH 7.4) buffer to the concentration of 120 μg/mL. Seventy five μL of the artificially prepared blood samples containing different concentrations of lymphocytes were incubated with 25 μL anti-CD45/Strep-AP premix and the samples were incubated for 15 min at RT. After incubation, 30 μl of each sample were placed using a pipette onto the LRF10S membrane (Pall, Port Washington, N.Y.) incorporated into the flow-through device. After each addition of sample, 500 μL of wash solution (10 mM TRIS (pH 7.4), 50 μg/mL NBT) were placed with a pipette onto the device five times to wash out the red blood cells. One hundred μL of alkaline phosphatase (AP) substrate (Hercules, Calif.) was added after washing. Ten min after adding the AP substrate, 200 μL of stop solution (0.1 N $H_2SO_4$) were added onto each of the membranes. Membranes were removed from the flow-through device and the color intensity was read using a portable reflectance colorimeter (FIA Biomed, Germany) as described in the Example 1. Total lymphocyte counts (CD45+ lymphocyte counts) were obtained using the traditional procedure for the total and differential WBC count by manual microscopy. The total WBC counts were determined by lysing red blood cells in 2% acetic acid solution and counting WBCs in the hemacytometer chamber. For the lymphocyte count, a blood smear stained with Wright solution (EMS, Hatfield, Pa.) was examined under microscope and the determined percentage of lymphocytes was used to calculate absolute count (Total lymphocyte count=Total WBC count×(% lymphocytes)/100). A plot of the color measurements (reflectance) versus the lymphocyte count in the range of 2,000 to 9,000 counts/μL is shown in FIG. 7.

Figure 6:
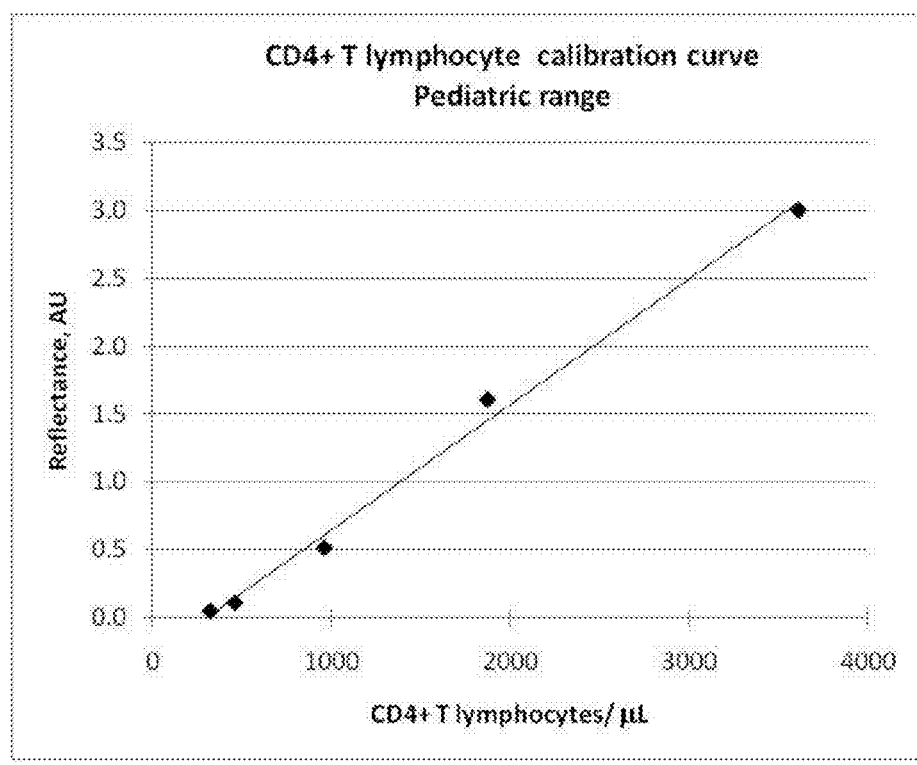
FIG. 6 shows the FTCA calibration curve for determination of CD4+ T-cell count for patients less than 5 years of age.
Figure 7:
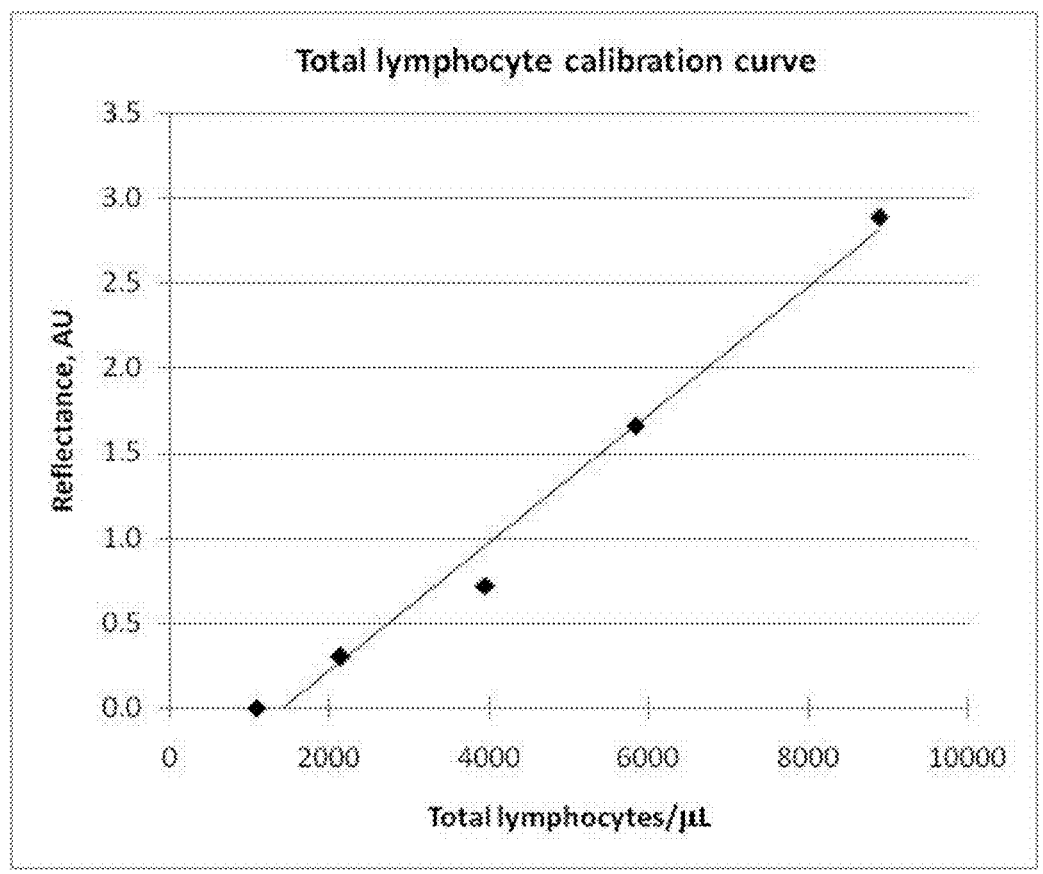
FIG. 7 shows the FTCA calibration curve for determination of total lymphocyte count for patients less than 5 years of age.

The CD4+ T-cell count and total lymphocytes count obtained using calibration curves presented in FIGS. 6 and 7, respectively can be used for calculation of the percentage of CD4+ T-cells for the given sample.

EXAMPLE 3

Determination of CD8+ T-Lymphocyte Count for Pediatric Patients

Figure 8:
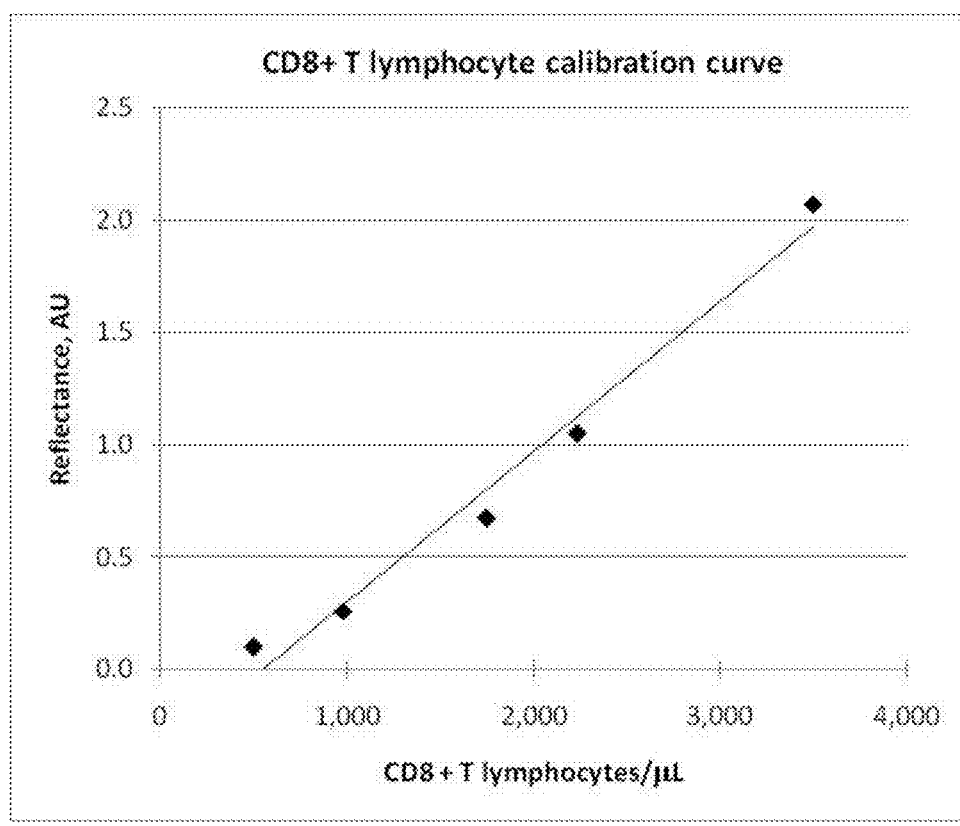
FIG. 8 shows the FTCA calibration curve for determination of CD8+ T-cell count for patients less than 5 years of age.

Sometimes, CD4/CD8 ratio is used to establish the level of immunodeficiency and make decisions when to start cotrimoxazole (CTX) prophylaxis and/or ART in all HIV infected children younger than 5 years of age. In order to do that, CD4+ and CD8+ T-cells counts must be determined. In this example, the calibration curve for determination of CD8+ T-cells was prepared using the following protocol 4: Undiluted anti-CD8antibody (BD Pharmingen, San Diego, Calif.) was premixed at 2:1 with Streptavidin-AP (Sigma, Saint Louis, Mo.) diluted in TRIS-buffered saline (TBS, pH 7.4) buffer to the concentration of 24 μg/mL and incubated at room temperature for 30 min. Seventy microliters of WBC-enriched blood, whole blood or CD3 depleted blood was incubated with 30 μL Strep-AP/anti-CD4 "conjugate" (anti-CD4 and Strep-AP premix) and the samples were incubated for 15 min at RT. Thirty microliters of each sample were added using a pipette onto the LRF10S membrane incorporated into the flow-through device. After each addition of the sample, 500 μL of wash solution (10 mM TRIS (pH 7.4), 50 μg/mL NBT) were added using a pipette onto the device five times to wash out the red blood cells. One hundred μL of alkaline phosphatase (AP) substrate (Hercules, Calif.) was added after washing procedure. Ten min after adding AP substrate, 200 μL of stop solution (0.1 N $H_2SO_4$) was added onto each of the membranes. Membranes were removed from the flow-through device and the color intensity was read using a portable reflectance colorimeter (FIA Biomed, Germany) as described in the Example 1. A plot of the color measurements (reflectance) versus the CD8+ T lymphocyte count obtained using Dynal® T4 quantification method (Invitrogen, Grand Island, N.Y.), using CD8 magnetic beads is shown in FIG. 8

Although the invention herein has been described with respect to particular embodiments, it is understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

REFERENCES

[1] Complete Blood Count (CBC) with Five-Part Differential. NHANES 2003-2004
[2] C. Briggs, S. Kimber, and L. Green, Where are we at with point-of-care testing in haematology? Br J Haematol 158 (2012) 679-90.
[3] I. V. Jani, N. E. Sitoe, P. L. Chongo, E. R. Alfai, J. I. Quevedo, O. Tobaiwa, J. D. Lehe, and T. F. Peter, Accurate CD4 T-cell enumeration and antiretroviral drug toxicity monitoring in primary healthcare clinics using point-of-care testing. AIDS 25 (2011) 807-12.
[4] F. Papa, M. Rongioletti, M. B. Majolini, V. Collegiani, C. Vaccarella, M. L. Notarmuzi, M. Cortesi, P. Pasqualetti, M. Cicchese, R. Agostino, and G. M. Liumbruno, Fast bedside measurement of blood count and C-reactive protein in newborns compared with conventional methods. Clin Lab 58 (2012) 951-7.
[5] R. J. Leguit, and J. G. van den Tweel, The pathology of bone marrow failure. Histopathology 57 (2010) 655-70.
[6] K. Asadollahi, N. J. Beeching, and G. V. Gill, Leukocytosis as a predictor for non-infective mortality and morbidity. QJM 103 (2010) 285-92.
[7] R. Chang, and G. Y. Wong, Prognostic significance of marked leukocytosis in hospitalized patients. J Gen Intern Med 6 (1991) 199-203.
[8] G. J. Despotis, V. Levine, and L. T. Goodnough, Relationship between leukocyte count and patient risk for excessive blood loss after cardiac surgery. Crit Care Med 25 (1997) 1338-46.
[9] L. Paladino, R. A. Subramanian, E. Bonilla, and R. H. Sinert, Leukocytosis as prognostic indicator of major injury. West J Emerg Med 11 (2011) 450-5.
[10] A. Osei-Bimpong, C. Jury, R. McLean, and S. M. Lewis, Point-of-care method for total white cell count: an evaluation of the HemoCue WBC device. Int J Lab Hematol 31 (2009) 657-64.
[11] B. A. Ekberg, U. D. Larsen, and N. Fogh-Andersen, A Real Point-of-Care System for Complete Blood Counting. Point of Care 4 (2005) 64-65.
[12] M. M. Wintrobe, and J. P. Greer, Wintrobe's Clinical Hematology, Lippincott Williams & Wilkins, Philadelphia, Pa., 2009.
[13] B. Houwen, The Differential Cell Count. Laboratory Hematology 7 (2001) 89-100.
[14] J. Embree, J. Bwayo, N. Nagelkerke, S. Njenga, P. Nyange, J. Ndinya-Achola, H. Pamba, and F. Plummer, Lymphocyte subsets in human immunodeficiency virus type 1-infected and uninfected children in Nairobi. Pediatr Infect Dis J 20 (2001) 397-403.
[15] S. B. Tugume, E. M. Piwowar, T. Lutalo, P. N. Mugyenyi, R. M. Grant, F. W. Mangeni, K. Pattishall, and E. Katongole-Mbidde, Hematological reference ranges among healthy Ugandans. Clin Diagn Lab Immunol 2 (1995) 233-5.

[16] W. M. Comans-Bitter, R. de Groot, R. van den Beemd, H. J. Neijens, W. C. Hop, K. Groeneveld, H. Hooijkaas, and J. J. van Dongen, Immunophenotyping of blood lymphocytes in childhood. Reference values for lymphocyte subpopulations. J Pediatr 130 (1997) 388-93.

[17] W. T. Shearer, H. M. Rosenblatt, R. S. Gelman, R. Oyomopito, S. Plaeger, E. R. Stiehm, D. W. Wara, S. D. Douglas, K. Luzuriaga, E. J. McFarland, R. Yogev, M. H. Rathore, W. Levy, B. L. Graham, and S. A. Spector, Lymphocyte subsets in healthy children from birth through 18 years of age: the Pediatric AIDS Clinical Trials Group P1009 study. J Allergy Clin Immunol 112 (2003) 973-80.

[18] World Health Organization. Antiretroviral therapy of HIV infection in infants and children in resource-limited settings: Towards universal access. Recommendations for a public health approach. 2006. Available at: http://www.who.int/hiv/pub/guidelines/WHOpaediatric.pdf.

[19] M. R. O'Gorman, and L. S. Zijenah, CD4 T cell measurements in the management of antiretroviral therapy—A review with an emphasis on pediatric HIV-infected patients. Cytometry B Clin Cytom 74 Suppl 1 (2008) S19-26.

[20] F. Lutwama, R. Serwadda, H. Mayanja-Kizza, H. M. Shihab, A. Ronald, M. R. Kamya, D. Thomas, E. Johnson, T. C. Quinn, R. D. Moore, and L. A. Spacek, Evaluation of Dynabeads and Cytospheres compared with flow cytometry to enumerate CD4+ T cells in HIV-infected Ugandans on antiretroviral therapy. J Acquir Immune Defic Syndr 48 (2008) 297-303.

[21] F. Garbassi, M. Morra, and E. Occhiello, Polymer surfaces: from physics to technology, John Wiley and Sons, New York, 1998.

[22] PointCare NOW™ Technical Note: Summary of Evaluation and Performance Data. PointCare Technologies, 2011.

[23] W. Stevens, R. Gelman, G. K. Glencross, L. E. Scott, S. M. Crowe, and T. Spira, Evaluating new CD4 enumeration technologies for resource-constrained countries. Nature Reviews Microbiology 6 (2008) S29-S38.

The invention claimed is:

1. A method for determining of at least one of CD4+ T-cell lymphocytes count, CD8+ T-cell lymphocytes count, or total lymphocytes count in a biological fluid sample, the method comprising the steps of:
(a) adding to said biological fluid sample a sole antibody specific to any one of said respective lymphocytes, said sole antibody conjugated with an optically detectable marker, said sole antibody is selected from the group consisting of an anti-CD4 antibody for determination of said CD4+ T-cell lymphocytes count, anti-CD8 antibody for determination of said CD8+ T-cell lymphocytes count, and an anti-CD45 antibody for determination of said total lymphocytes count;
(b) incubating said biological fluid sample mixture of step (a) for duration from about 5 min to about 60 min and at a temperature ranging from about 20 degrees Celsius to about 37 degrees Celsius;
(c) filtering said biological fluid sample mixture through a leukocyte-reduction retainer filter, said filter is configured for capturing thereon of said all leukocytes including those which bound to said antibody of said biological fluid sample mixture, said filter is further configured for all captured leukocytes to contain at least 80 percent or more lymphocytes and at least 20 percent or less of any other subsets of leukocytes;
(d) washing said leukocyte-reduction retainer filter to remove weakly-bound substances; and
(e) optically detecting said bound antibody conjugated to said optically detectable marker which is retained on said leukocyte-reduction retainer filter in step (c) to determine of said at least one respective CD4+ T-cell lymphocytes count, CD8+ T-cell lymphocytes count, or total lymphocytes count in said biological fluid.

2. The method of claim 1, wherein the optically detectable marker is selected from the group consisting of an enzyme, an enzyme complex, a plurality of gold microparticles, a plurality of quantum dot microparticles, a plurality of fluorescent latex microparticles, a plurality of fluorescent liposomes, a fluorescent dye, a photochemical dye, an chemiluminescent compound, and an electrochemiluminescent compound.

3. The method of claim 1, wherein said optically detectable marker is a biotin and said step (a) further includes adding of a streptavidin conjugate or an avidin conjugate of a material selected from the group consisting of an enzyme, an enzyme complex, a plurality of gold microparticles, a plurality of quantum dot microparticles, a plurality of fluorescent latex microparticles, a plurality of fluorescent liposomes, a fluorescent dye, a photochemical dye, a chemiluminescent compound, and a electrochemiluminescent compound.

4. The method of claim 1, wherein in said step (d) said optically detectable marker is detected by analyzing color intensity by eye or by using an optical instrument or by using an electrochemical instrument.

5. The method as in claim 4, wherein said optical instrument or said electrochemical instrument is selected from the group consisting of a reflectometer, a photometer, a fluorimeter, a chemiluminometer, and an electrochemical reader.

6. The method of claim 1 further comprising a step of calculating at least one of a ratio of CD4+ T cells count to total lymphocytes count or a ratio of CD4+ T cells count to CD8 lymphocytes count or a ratio of CD8 lymphocytes count to total lymphocytes count.

7. The method of claim 1, wherein said optically detectable marker is an Alkaline Phosphatase.

8. The method of claim 1, wherein said optically detectable marker is a biotin and said step (a) further includes adding of a streptavidin—Alkaline Phosphatase or an avidin—Alkaline Phosphatase conjugate to said biological fluid sample mixture.

9. The method of claim 8, wherein after said step (d) of washing said retainer filter and before said step (e) of optically detecting said marker there is included an additional step of adding an Alkaline Phosphatase substrate solution.

10. The method as in claim 9, wherein said Alkaline Phosphatase substrate solution is selected from the group consisting of a chromogenic substrate, a fluorogenic substrate, a chemiluminescent substrate, and a electrochemiluminescent substrate.

11. The method as in claim 10, wherein:
said chromogenic substrate is selected from the group consisting of 5-Bromo-4-chloro-3-indolyl phosphate/ p-iodonitrotetrazolium (BCIP/INT); 6-chloro-3-indoxyl phosphate, p-toluidine / NBT (BCIP pink/NBT); 3-indoxyl phosphate/ NBT; Fast Red TR/ Naphthol AS-MX phosphate; Fast Red TR/ Naphthol AS-TR phosphate; and p-nitrophenol phosphate (pNPP);
said fluorogenic substrate is selected from the group consisting of 4-methylumbelliferyl phosphate (4-MUP); 6,8-Difluoro-4-methylumbelliferyl phosphate (DiFMUP); Fluorescein diphosphate (FDDP); 2'-[2- benzthiazoyl]-6'-hydroxy-benzthiazole (BBTP); 2-(5'-chloro-2-phosphoryloxyphenyl) -6-chloro-4(3H)-quinazolinone (ELF 97); Acridinium (N-sulfonyl) carboxamide and acridinium ester-based substrates; and Rhodamine 110-based phosphates;

said chemiluminescent substrate is selected from the group consisting of Acridinium (N-sulfonyl) carboxamide and acridinium ester-based substrates; 1,2 Dioxetane-based substrates (4-methoxy-4-(3-phosphatephenyl)spiro[1,2-dioxetane-3,2'-adamantane]; and disodium salt-based substrates (AMPPD); and said electrochemiluminescenct substrate is a ruthenium salt-based substrate.

12. The method of claim 9, wherein said step (e) including detecting a chromogenic signal or a fluorogenic signal or a chemiluminescent signal or an electrical signal, said detecting is done either visually by eye or by using an optical instrument or by using an electrochemical instrument.

13. The method as in claim 1, wherein said biological fluid sample is selected from the group consisting of a whole blood and a blood fraction.

14. The method of claim 13, wherein said blood fraction is selected from a the group consisting of a buffy coat, and a whole blood cell fraction.

15. The method of claim 1, wherein said antibody is added in the step (a) in a lyophilized freeze-dried form.

16. The method of claim 1, wherein in said step (d) said optically detectable marker is detected by analyzing color intensity, the marker is selected from the group consisting of an enzyme, an enzyme complex, a plurality of gold microparticles, a plurality of quantum dot microparticles, and a plurality of fluorescent latex microparticles.

17. The method of claim 1, wherein in said step (d) said optically detectable marker is detected by analyzing color intensity, said optically detectable marker is a biotin and said step (a) further includes adding of a streptavidin conjugate or an avidin conjugate of a material selected from the group consisting of an enzyme, an enzyme complex, a plurality of gold microparticles, a plurality of quantum dot microparticles, a plurality of fluorescent latex microparticles.

* * * * *